US012667127B2

(12) United States Patent
Marchal et al.

(10) Patent No.: US 12,667,127 B2
(45) Date of Patent: Jun. 30, 2026

(54) ACETOBACTER FOR USE IN PREPARATION OF FERMENTED PRODUCTS

(71) Applicant: Compagnie Gervais Danone, Paris (FR)

(72) Inventors: Laurent Marchal, Villemoisson sur Orge (FR); Peggy Garault, Montlhery (FR); Marie-Christine Degivry, Le Plessis Robinson (FR); Christophe Daval, Palaiseau (FR)

(73) Assignee: Compagnie Gervais Danone, Paris (FR)

( * ) Notice: Subject to any disclaimer, the term of this patent is extended or adjusted under 35 U.S.C. 154(b) by 404 days.

(21) Appl. No.: 18/255,175

(22) PCT Filed: Dec. 3, 2021

(86) PCT No.: PCT/IB2021/000843

§ 371 (c)(1),
(2) Date: May 31, 2023

(87) PCT Pub. No.: WO2022/118075

PCT Pub. Date: Jun. 9, 2022

(65) Prior Publication Data

US 2024/0023591 A1     Jan. 25, 2024

Related U.S. Application Data

(60) Provisional application No. 63/121,281, filed on Dec. 4, 2020.

(51) Int. Cl.
*A23L 33/135*     (2016.01)
*A23F 3/16*     (2006.01)
*A23L 2/38*     (2021.01)
*A23L 33/14*     (2016.01)
*C12N 1/205*     (2026.01)
*C12R 1/02*     (2006.01)

(52) U.S. Cl.
CPC ............ *A23L 33/135* (2016.08); *A23F 3/166* (2013.01); *A23L 2/382* (2013.01); *A23L 33/14* (2016.08); *C12N 1/205* (2021.05); *C12R 2001/02* (2021.05)

(58) Field of Classification Search
None
See application file for complete search history.

(56) References Cited

U.S. PATENT DOCUMENTS

2020/0352190 A1* 11/2020 Johnson ..................... C12J 1/08

FOREIGN PATENT DOCUMENTS

| CN | 111057722 A | * | 4/2020 | ............... C12P 1/02 |
| EP | 3563693 A1 | | 11/2019 | |
| KR | 20110111157 A | | 10/2011 | |

OTHER PUBLICATIONS

Ayed et al., "Development of a beverage from red grape juice fermented with the Kombucha consortium", Nov. 26, 2016, vol. 67, No. 1, p. 111-121.
International Search Report mailed Mar. 15, 2022, issued in PCT/IB2021/000843.

* cited by examiner

*Primary Examiner* — Erik Kashnikow
*Assistant Examiner* — Thanh H Nguyen
(74) *Attorney, Agent, or Firm* — ArentFox Schiff LLP

(57)     ABSTRACT

The present invention relates to a novel strain of *Acetobacter malorum*, compositions comprising said strain and to methods for the preparation of such compositions.

12 Claims, No Drawings

ACETOBACTER FOR USE IN PREPARATION OF FERMENTED PRODUCTS

CROSS-REFERENCE TO RELATED APPLICATIONS

This application is a National Phase of PCT Application No. PCT/IB2021/000843, filed Dec. 3, 2021, which claims priority to U.S. Provisional Application No. 63/121,281, filed Dec. 4, 2020, the disclosures of each of which are hereby incorporated by reference in their entirety.

FIELD OF THE INVENTION

The present invention relates to a novel strain of *Acetobacter malorum*, compositions comprising said strain and to methods for the preparation of such compositions.

TECHNICAL BACKGROUND

There is increased interest in probiotic food products such as beverages among consumers. According to a definition approved by a joint Food and Agriculture Organization of the United Nations/World Health Organization (FAO/WHO) expert Consultation on Health and Nutritional properties of powder milk with live lactic acid bacteria in 2001, probiotics are "live microorganisms which when administered in adequate amounts confer a health benefit on the host". However, the addition of such species, especially in the context of fermented food products can be challenging as they can introduce undesirable flavours or off-notes to products. The formulation of such products to provide a good shelf life while maintaining high levels of live and active cultures also remains challenging.

Fermented beverages such as kombucha and water kefir are increasingly popular with health-minded consumers who appreciate the potential probiotic benefits of such beverages.

Traditionally such beverages are prepared by fermenting an aqueous base with symbiotic micro-organisms. Kombucha is a lightly sparkling sweetened tea, characterized by a slight vinegary tanginess that is fermented by means of a symbiotic culture of yeast and acetic-acid producing bacteria encase in a biofilm commonly referred to as a SCOBY, mother or mushroom.

Home brewed kombuchas are usually prepared by brewing a tea base to which sugars and fruit can be added and fermenting by means of the SCOBY typically for several days (e.g. 1-2 weeks) at room temperature. Commercial kombuchas are typically pasteurized or otherwise heat treated to inactivate the SCOBY thus allowing for an improved shelf life.

EP0791296 provides a method for the preparation of a fermented tea beverage, using an inoculant of yeast and bacteria and fermenting under aerobic conditions. However, the fermented tea beverage prepared according to this patent has a relatively low acetic acid concentration and in the process insoluble are removed and the beverage is heat-treated, the beverage thus would not contain live and active cultures.

U.S. Pat. No. 8,697,055 discloses a composition comprising the probiotic *Bacillus coagulans* and tea (e.g. a tea bag), it fails to disclose a fermented beverage and thus it appears that the composition taught does not contain the beneficial byproducts of fermentation (often referred to as postbiotics)

nor does it have the characteristic composition and organoleptic qualities of fermented tea (e.g. acetic acid).

SUMMARY OF THE INVENTION

The present invention follows from the unexpected finding that the novel strain of *Acetobacter malorum* CNCM I-5329 can be used to prepare a fermented tea having a good level of acetic acid after a relatively quick fermentation time.

Accordingly, the present invention provides *Acetobacter malorum* strain deposited at the CNCM under reference numbers CNCM I-5329. The present invention also provides compositions comprising *Acetobacter malorum* CNCM I-5329 and methods for the preparation thereof.

DETAILED DESCRIPTION OF THE INVENTION

As used herein, the term "ppm" shall be taken to mean "parts per million". One millilitre in 1 liter is 1000 ppm and one thousandth of a millilitre (0.001 g) in 1 liter is one ppm.

As used herein, the term "x % (w/w)" or "x % w/w" is equivalent to "x g per 100 g". Unless indicated otherwise, all % value shall be taken to indicate x % w/w.

As used herein, the term "x % (v/v)" or "x % v/v" is equivalent to "x ml per 100 ml".

In the context of the invention, the term "at least" also includes the starting point of the open range. For example, an amount of "at least 95.00% w/w" means any amount equal to 95.00 percentage by weight or above.

In the context of the invention, the term "about" defines a range of plus or minus 10% of the cited value. For example, an amount of "about 20 weight %" means any amount within the range of 18.00 to 22.00 weight %.

As used herein, the terms "vegan", "plant-based" or "plant based" shall be taken to mean a composition or product which comprises plant or plant-derived matter but which does not comprise animal or animal-derived (e.g. mammal milk) matter.

As used herein, the adjective "dairy" shall be taken to mean a composition or product comprises or consists of mammalian milk matter, i.e. the lacteal secretion obtainable by milking.

As used herein, the terms "-free" or "free from" shall be taken to mean a composition or product which preferably does not contain a given substance but where trace amounts or contaminants thereof may be present.

As used herein, the term "added sugar" shall refer to sugars that are added during the processing of foods (e.g. refined sugars that may be added to a vegetal base of processed plant matter) as opposed to sugars naturally occurring in said foods. Added sugars include sugars (free, mono- and disaccharides), sugars from syrups and honey, and sugars from concentrated fruit or vegetable juices that are in excess of what would be expected from the same volume of 100 percent fruit or vegetable juice of the same type.

As used herein, the term "fermented plant-based" shall be taken to mean a product or composition that is the product of the acidifying fermentation of a plant-based composition by a starter culture of fermenting microorganisms, in particular yeast, bacteria and or combinations thereof.

As used herein, the term "fermented dairy milk" shall be taken to mean a product or composition derived from dairy milk by the acidifying action of at least one lactic acid bacterium, such as a yogurt (e.g., a set, stirred or drink yogurt), or a fresh cheese such as a white cheese or a "petit-Suisse". It can also be a strained fermented milk such as a strained yoghurt (e.g., a concentrated or Greek-style yoghurt).

As used herein, the terms "plant-based alternative", "analogue" or "substitute" shall be taken to mean a plant-based food or beverage composition that is formulated to simulate the organoleptic and/or nutritional qualities of a non plant-based product. Accordingly, a "plant-based fermented milk alternative" shall be taken to mean a plant-based food or beverage composition that is formulated to simulate the organoleptic and/or nutritional qualities of fermented dairy milk. A "plant-based yogurt" shall be taken to mean a plant-based food or beverage composition that is formulated to simulate the organoleptic and/or nutritional qualities of fermented dairy yogurt.

The term "dairy yogurt" or "plant-based yogurt" as used herein shall be taken to mean fermented dairy or plant-based milk respectively obtained by the acidifying lactic fermentation of the bacteria *Lactobacillus delbrueckii* subsp. *bulgaricus* and *Streptococcus thermophilus* (also referred to as *Streptococcus salivarius* subsp. *thermophilus*), which must be viable in the finished product at a minimum CFU. In certain countries, regulations allow the addition of further lactic acid bacteria to yoghurt such as, but not limited to, strains of *Bifidobacterium* and/or *Lactobacillus acidophilus* and/or *Lactobacillus casei*. These additional lactic acid bacteria strains are intended to impart various properties to the finished product, such as that of providing organoleptic qualities, favoring equilibrium of intestinal flora or modulating the immune system.

As used herein, the term "strained" shall be taken to mean a fermented composition which has been subjected to a post-fermentation separation process.

As used herein, the term "spoonable" shall be taken to mean a solid or semi-solid that may be consumed by means of a spoon or other utensil.

As used herein the term "beverage" shall be taken to mean a potable liquid or semi-liquid that may be consumed by means of drinking.

As used herein, the term "fermentation" shall be taken to mean the metabolism of a substance by microorganisms, e.g. bacteria, yeasts, or other microorganisms.

As used herein the term "viable" when used in reference to a micro-organism shall be taken to mean a metabolically and physiologically active micro-organism, means for the detection of viability in micro-organisms are known in the art and include plate count and flow cytometry based methods.

As used herein, the term "cfu" or "CFU" shall be taken to be an abbreviation of the term "colony forming unit".

As used herein reference to a bacterial strain or species shall be taken to include functionally equivalent bacteria derived therefrom such as but not limited to mutants, variants or genetically transformed bacteria. These mutants or genetically transformed strains can be strains wherein one or more endogenous gene(s) of the parent strain has (have) been mutated, for instance to modify some of their metabolic properties (e.g., their ability to ferment sugars, their resistance to acidity, their survival to transport in the gastrointestinal tract, their post-acidification properties or their metabolite production). They can also be strains resulting from the genetic transformation of the parent strain to add one or more gene(s) of interest, for instance in order to give to said genetically transformed strains additional physiological features, or to allow them to express proteins of therapeutic or prophylactic interest that one wishes to administer through said strains. These mutants or genetically transformed strains can be obtained from the parent strain by means of conventional techniques for random or site-directed mutagenesis and genetic transformation of bacteria, or by means of the technique known as "genome shuffling". In the present text, strains, mutants and variants derived from a parent species or strain will be considered as being encompassed by reference to said parent species or strain, e.g. the phrases "*Acetobacter malorum*" and "CNCM I-5329" shall be taken to include strains, mutants and variants derived therefrom. Accordingly, as used herein reference to a bacterial strain specified by an accession or deposit number shall be taken to encompass variants thereof having at least 95% identity (see: Stackebrandt & Goebel, 1994, Int. J. Syst. Bacteriol. 44:846-849). In a particularly preferred embodiment, said variant has at least 97% identity with the 16S rRNA sequence of said specified strain, more preferably at least 98% identity, more preferably at least 99% or more identity.

As used herein the term "substantially pure" when used in reference to a bacterial strain refers to the percent of said bacterial strain relative to the total micro-organism content. Substantially pure can be at least about 99.99%, at least about 99.90%, at least about 99.50%, at least about 99.00%, at least about 95.00%, at least about 90.00%, at least about 85.00%, or at least about 75.00%.

As used herein, a "lactic acid bacterium" is a Gram-positive, acid-tolerant, generally non-sporulating and non-respiring, either rod- or cocci-shaped bacterium that is able to ferment sugars into lactic acid.

As used herein an "*Acetobacter*" is a gram-negative acetic acid bacteria characterized by the ability to convert ethanol to acetic acid.

The present invention relates to novel strains of *Acetobacter malorum*, compositions comprising said strain and to methods for the preparation of such compositions.

*Acetobacter malorum*

In a first aspect, the present invention provides a strain of *Acetobacter malorum*. In a first embodiment, the present invention provides the strain *Acetobacter malorum* CNCM I-5329. This strain has been deposited at the Collection Nationale de Cultures de Microorganismes (CNCM) (Institut Pasteur, 25 Rue du Docteur Roux, 75724 Paris, France) under the Budapest Treaty on 12 Jun. 2018 under reference number CNCM I-5329. The deposit was made in accordance with the Budapest Treaty on the International Recognition of the Deposit of Microorganisms for the Purposes of Patent Procedure, as provided therein the applicant requests that a sample of the deposited micro-organisms only be made available to an independent expert, until the date on which the patent may be granted. In one embodiment, the present invention provides the isolated strain *Acetobacter malorum* CNCM I-5329, preferably said isolate is substantially pure.

Compositions of the Invention

In a second aspect, the present invention provides compositions comprising *Acetobacter malorum* CNCM I-5329. Preferably, the composition comprises at least $10^1$, $10^2$, $10^3$, $10^4$, $10^5$ or $10^6$ cfu colony forming unit (CFU) *Acetobacter malorum* CNCM I-5329 per gram (g) of composition according to embodiments of the invention.

In embodiments, the composition comprises $10^1$ to $10^{17}$ colony forming unit (CFU) *Acetobacter malorum* CNCM I-5329 per gram (g) of composition according to embodiments of the invention. In further embodiments, the composition comprises $10^3$ to $10^5$ colony forming unit (CFU)

*Acetobacter malorum* CNCM I-5329 per gram (g) of composition according to embodiments of the invention.

The bacterium as provided herein is suitable for use in edible compositions, accordingly in one embodiment the present invention provides a composition suitable for human consumption or ingestion, preferably by oral means. Accordingly the composition comprises or consists of comestible matter. It is particularly preferred that the compositions of embodiments of the invention are substantially free of pathogenic or toxicogenic matter. The composition according to embodiments of the invention may be a medicament or pharmaceutical composition. In a particularly preferred embodiment the composition according to the invention may be a non-therapeutic composition, preferably a nutraceutical composition, a nutritional composition and/or a food composition. It is particularly preferred that the food composition is a fermented food composition, preferably a product.

The composition may comprise further additional strains of yeast and/or lactic acid bacteria; typically 1, 2, 3, 4 or more additional strains. In embodiments, the yeast comprises 1, 2 or more species of the genera selected from the group consisting of *Brettanomyces, Hansenispora, Torulaspora* and *Saccharomyces* and/or mixtures or combinations thereof. In further embodiments the yeast comprises 1, 2 or more species selected from the group consisting of *Brettanomyces bruxellensis, Hanseniaspora osmophila, Hanseniaspora valbyensis, Torulaspora* sp., *Saccharomyces cerevisiae* and *Saccharomyces uvarum* and/or mixtures or combinations thereof. It is particularly preferred that the yeast is *Saccharomyces cerevisiae.*

In embodiments, the bacteria comprises 1, 2 or more species of the genera selected from the group consisting of *Gluconobacter, Oenococcus, Acetobacter, Bacillus, Lactobacillus* and *Lactococcus* and/or mixtures or combinations thereof. In further embodiments the bacteria comprises 1, 2 or more species selected from the group consisting of *Gluconobacter cerinus, Oenococcus kitaharae, Acetobacter Malorum, Acetobacter Lambici, Bacillus coagulans, Lactobacillus nagelii, Lactobacillus paracasei, Lactobacillus hilgardii, Lactobacillus hordei, Lactobacillus plantarum, Lactococcus lactis lactis, Lactococcus lactis cremoris* and *Lactococcus taiwanensis* and/or mixtures or combinations thereof.

Accordingly in one embodiment the present invention provides a composition comprising *Acetobacter malorum* CNCM I-5329 and further comprising at least one strain of yeast.

In embodiments the bacteria and yeast are not physically joined by an extracellular matrix secreted by said microorganisms, such as a cellulose biofilm (e.g. kombucha "mother" or SCOBY, for Symbiotic Community of Bacteria and Yeast) or polysaccharide matrix grains (such as but not limited to dairy kefir grains or water kefir grains).

Plant-Based Compositions.

The strain of the present invention is particularly suited to the preparation of fermented compositions. Accordingly, in one embodiment, the present invention provides a plant-based composition comprising CNCM I-5329, preferably a product. The plant-based composition of the invention comprises fruit or vegetable matter, preferably fermented. Accordingly, in embodiments, the present invention provides a product comprising i) an aqueous base ii) CNCM I-5329 and optionally iii) yeast.

In embodiments the composition is a fermented food product, preferably a beverage. The fermented beverage according to embodiments of the invention is preferably a kombucha type beverage, water kefir type beverage, jun type beverage, tibicos type beverage, drinking vinegar beverage or equivalents thereof. In embodiments, the fermented beverage is not a plant-based dairy alternative, analogue or substitute.

In one embodiment, the aqueous vegetal base is an aqueous suspension comprising water and plant-matter preferably selected from the group consisting of fruits, herbs, spices, flowers, tea and/or combinations or mixtures thereof.

Processes for the preparation of such suspensions are known in the art and typically comprise mixing or combining aqueous solution with the plant matter and heat treating. Optionally, processes for preparation may include a step of removing insoluble solids before or after heat treatment, methods for such removal are known in the art and may be carried out by means of filtration, centrifugation and/or decantering.

Preferably the heat treatment is carried out at a temperature of less than or equal to 100° C. for a time sufficient to ensure that the product is safe to consume after fermentation. In embodiments the heat treatment is carried out at 70° C. to 100° C., more preferably 80° C. to 100° C. It is within the scope of the skilled person to adjust the time of heat treatment according to the selected temperature, but such treatments may be carried out for less than about 10, 9, 8, 7, 6 or 5 minutes e.g. about 0.1 to about 10 minutes or about 2 to about 5 minutes.

In embodiments, the aqueous vegetal base comprises water in an amount of from 99.99% to 20.0% by weight, preferably 99.99% to 50.0% or more preferably 99.99% to 60.0% or 99.99% to 70.0%.

In embodiments, the aqueous vegetal base comprises added sugars in an amount of 0.01% to 10.00% by weight. In embodiments the aqueous vegetal base comprises plant matter in an amount of from 0.01% to 80.00% by weight, preferably 0.01% to 50.00% or more preferably 0.01% to 20.00% or 0.01% to 10.00%.

The aqueous base can for example comprise fruit or a fruit preparation in an amount of from 0.1% to 80.00% by weight, for example from 0.1% to 50.00% or 10.00% to 50.00% by weight. Accordingly, in embodiments, the vegetal base comprises fruit. Fruit preparations typically comprise fruits, as used herein the term "fruit" refers to any fruit form, including for example full fruits, pieces, purees, concentrates, juices etc.

Examples of fruits include for example lemon, fig, strawberry, peach, apricot, mango, apple, pear, raspberry, blueberry, blackberry, passion, cherry, and mixtures or associations thereof, such as peach-passion.

The fruits can be for example provided as:

fruit juices or concentrates thereof, for example fruit juices concentrated from 2 to 5 times, preferably 3 times, for example aseptic fruit juices, for example strawberry, peach, apricot, mango, raspberry, blueberry or apple fruit purees or mixtures thereof, dried fruit whole, cubes or in pieces, for example dried whole figs or mixtures thereof, frozen fruit whole, cubes or in pieces, for example 10 mm fruit cubes, for example Individual Quick Frozen fruit cubes, for example strawberry, peach, apricot, mango, apple, pear fruit cubes or mixtures thereof, Aseptic fruit cubes, for example 10 mm fruit cubes, for example strawberry, peach, apricot, mango, apple or pear fruit cubes or mixtures thereof, fruit purees or concentrates thereof, for example fruit purees concentrated from 2 to 5 times, preferably 3 times, for example aseptic fruit purees, for example strawberry, peach, apricot, mango, raspberry, blueberry or apple fruit purees or mixtures thereof, single aseptic fruit purees, for example strawberry, raspberry, peach, apricot, blueberry or apple single aseptic fruit purees or mixture thereof, frozen whole fruits, for example Individual Quick Frozen whole fruits, for example blueberry, raspberry or blackberry frozen whole fruits, or mixtures thereof, mixtures thereof.

The aqueous base can comprise tea, herbs, flowers and/or combinations or mixtures thereof in an amount of 0.01% to 10.00% by weight, for example from 0.01% to 5.00% by weight or 0.01% to 2.00%.

The tea, herbs and flowers may be in fresh, dried, frozen or freeze dried form or may be in the form of extracts, concentrates or infusions.

In one embodiment, the fermented beverage according to embodiments of the invention is a kombucha type beverage prepared by the fermentation of an aqueous tea base. Accordingly in embodiments the vegetal base comprises tea. Methods for the preparation of tea are well known in the art. The aqueous tea base may be prepared by the steeping or soaking of tea leaves in water and combining with fruit and/or added sugars to provide a fermentable base. The tea may be black, white, green or red and may be in fresh or dried form. The tea leaves may be whole, ground and/or powdered.

In an alternative embodiment the aqueous tea base may be provided by dilution of a tea extract and/or liquid concentrate in water.

In embodiments of the invention the vegetal base does not comprise soy, nuts, seeds, grains and/or combinations or mixtures thereof. Particularly preferred is a base free from, or do not comprise, added sugar, where the total carbohydrate content of the vegetal base is derived from plant-matter selected from the group consisting of fruits, herbs, flowers, tea and/or combinations or mixtures thereof.

The fermented beverage may optionally comprise other ingredients such as fermentation aids (such as yeast extract or polypeptides), emulsifiers, stabilizing and flavoring agents. Other ingredients may also include nutritional supplements, vitamins, minerals, trace elements or other micronutrients. such as vitamin A, vitamin B2, vitamin B12, vitamin D, vitamin E, zinc, fiber, protein, calcium, potassium, phosphorus, fatty acids, (e.g., omega 3, omega 6, etc.).

Preferably, the fermented beverage has a pH equal to or lower than 5, 4.5, 4.0 or 3.5. In embodiments, the fermented beverage has a pH preferably between about 4 and about 2.5, and more preferably between about 3.5 and about 2.5.

The fermented beverage according to embodiments of the invention is preferably a kombucha type beverage, water kefir type beverage, jun type beverage, tibicos type beverage, drinking vinegar beverage or equivalents thereof. In embodiments, the fermented beverage is not a plant-based dairy alternative, analogue or substitute.

In one embodiment, the fermented beverage is a strained fermented beverage.

Preferably, the composition according to embodiments of the invention may be stored, transported and/or distributed at a temperature of from 1° C. to 10° C. for at least about 30 days, at least about 60 days or at least about 90 days from packaging and remain suitable for consumption.

In embodiments, the compositions of the invention comprise at least about $10^1$, $10^2$, $10^3$, $10^4$, $10^5$ or $10^6$ *Acetobacter malorum* CNCM I-5329 per gram of composition. In embodiments, the compositions of the invention comprise between $10^1$ to $10^7$, $10^2$ to $10^6$, $10^3$ to $10^5$ colony forming unit (CFU) *Acetobacter malorum* CNCM I-5329 per gram of composition.

Preferably, the composition is a packaged product that comprises between $10^1$ to $10^7$, $10^2$ to $10^6$, $10^3$ to $10^5$ colony forming unit (CFU) of *Acetobacter malorum* CNCM I-5329 per gram (gm) of product subsequent to packaging and during storage, transport and/or distribution at a temperature of less than 25° C., preferably from 1° C. to 10° C. for about at least about 90 days, at least about 120 days, at least about 180 days, or at least about 210 days or at least about 240 days.

Preferably, the product is a packaged product that comprises at least about $10^1$, $10^2$, $10^3$, $10^4$, $10^5$ or $10^6$ cfu/ml colony forming unit (CFU) each of *Acetobacter malorum* CNCM I-5329 per gram (gm) of product subsequent to packaging and during storage, transport and/or distribution at a temperature of less than 25° C., preferably from 1° C. to 10° C. for about at least about 90 days, at least about 120 days, at least about 180 days, or at least about 210 days or at least about 240 days.

Preferably, the fermented beverage, according to embodiments of the invention is provided in a sealed or sealable container containing about 50 ml (or 50 g) to 2 L (or 1 kg), for example a container of 50 ml (or 50 g) to 80 ml (or 80 g), or 80 ml (or 80 g) to 100 ml (or 100 g), or 100 ml (or 100 g) to 125 ml (or 125 g), or 125 ml (or 125 g) to 150 ml (or 150 g), or 150 ml (or 150 g) to 200 ml (or 200 g), or 200 ml (or 200 g) to 250 ml (or 250 g), or 250 ml (or 250 g) to 300 ml (or 300 g), or 300 ml (or 300 g) to 500 ml (or 500 g), or 500 ml (or 500 g) to 750 ml (or 750 g), or 750 ml (or 750 g) to 1 l (or 1 kg), or 1 l (or 1 kg) to 2 l (or 2 kg) product by volume (or weight).

In other embodiments, the fermented beverage is provided in a sealed or sealable container containing about 50 ml to 500 ml, 60 ml to 500 ml, 70 ml to 500 ml, 75 ml to 500 ml, 80 ml to 500 g, 85 ml to 500 ml, 90 ml to 500 ml, 95 ml to 500 ml, 100 ml to 500 ml, 105 ml to 500 ml, 110 ml to 500 ml, 115 ml to 500 ml, 120 ml to 500 ml, 125 ml to 500 ml, 130 ml to 500 ml, 135 ml to 500 ml, 140 ml to 500 ml, 145 ml to 500 ml, 150 ml to 500 ml, 200 ml to 500 ml, 300 ml to 500 ml, 320 ml to 500 g or 500 g product by weight. In other embodiments, the fermented beverage is provided in a sealed or sealable container containing about 1 oz to 12 oz, 2 oz to 12 oz, 3 oz to 12 oz, 4 oz to 12 oz, 5 oz to 12 oz, 6 oz to 12 oz or 12 oz product by volume.

The container can be any suitable beverage container, such as a cup, a can, a bottle, a carton or "brick" packaging, or a flexible container such as a pouch. The container is the packaging of the fermented beverage. The container typically presents an opening and a body. The opening can be sealed by sealing means such as a cap, a flexible lid or a rigid lid. In one embodiment the opening and/or sealing means is a tearable or detachable part of the container.

The container can be made of a material, optionally layered, comprising plastics, preferably recyclable and/or recycled, paper and/or metal, or glass.

Inoculum Compositions

The bacterium as described herein is useful as starter culture in the preparation of food compositions or products, such as product. Accordingly, in one embodiment the present invention provides an inoculum comprising *Acetobacter malorum* CNCM I-5329 that is suitable for the preparation of fermented food products. The inoculum of the invention is suitable for the direct inoculation *Acetobacter malorum* CNCM I-5329 into an aqueous base to provide product of the invention, typically without the need for a culture step prior to the said direct inoculation.

Typically, the inoculum further comprises excipient or carriers, the selection of which is within the scope of the skilled person but may include buffers or culture media. The inoculum may optionally comprise further components such as cryoprotectants, preservatives and/or additives including nutrients such as yeast extracts, cysteine, sugars and vitamins.

Typically, the inoculum is for use in the preparation of product, according in one embodiment the inoculum of the invention may be provided to the aqueous base in quantities of up to about 500 mg/l.

Typically, the inoculum is fresh, frozen, dried or lyophilized. The inoculum may be in liquid, dry, spray-dried or solid form. It is particularly preferred that the inoculum is in granular or liquid form. The inoculum may be defrosted and/or dispersed in liquid (e.g. water) prior to inoculation.

In embodiments, the inoculum comprises at least $10^9$ cfu, e.g. at least $10^{10}$ cfu, such as at least $10^{11}$ cfu *Acetobacter malorum* CNCM I-5329 per gram of inoculum composition. In embodiments, the inoculum comprises $10^9$ to $10^{12}$ colony forming unit (CFU), or more preferably $10^{10}$ to $10^{12}$ colony forming unit (CFU) *Acetobacter malorum* CNCM I-5329 per gram of inoculum.

Preferably the inoculum comprising *Acetobacter malorum* CNCM I-5329 is substantially pure.

In a further embodiment, the present invention provides a mixture or kit of parts of the inoculum of the invention together with inoculum of yeast (*saccharomyces*). In embodiments the mixture or kit of parts comprises multiple strains of micro-organisms characterized in that said organisms are not joined by an extracellular secreted matrix such as a cellulose biofilm (e.g. kombucha "mother" or SCOBY, for Symbiotic Community of Bacteria and Yeast) or polysaccharide matrix grains (such as but not limited to dairy kefir or water kefir grains).

Accordingly, in one embodiment, the present invention provides an inoculum mixture comprising a *Acetobacter malorum* CNCM I-5329 inoculum and further comprising at least one inoculum of yeast.

Methods for the Preparation of a Product

The bacteria as provided herein are suitable for use in the preparation of a food composition. Accordingly in a third aspect the present invention also relates to the intended use of *Acetobacter malorum* CNCM I-5329 for the preparation of a product.

The processes of the invention may be carried out as a process comprising the following steps:

a) providing a mixture comprising:
    i) dairy and/or aqueous vegetal base,
    ii) bacteria comprising CNCM I-5329,
    iii) optionally yeast, and
b) fermenting the mixture to provide a reduction in pH and/or sugar,
c) optionally packaging the fermented product.

a) Mixture i) Dairy Base

In embodiments, the composition is prepared using a dairy base comprising dairy milk. Preferably the base comprises at least about 30% (w/w) milk, more preferably at least about 50% (w/w) milk and even more preferably at least about 70% (w/w) milk. In embodiments, the base comprises at 30% to 100% (w/w) milk. In embodiments, base comprises 50% to 100% (w/w) milk. In embodiments, the base comprises 70% to 100% (w/w) milk. Preferably, said milk is animal milk, more preferably goat, ewe, camel, mare or cow milk, and most preferably to cow milk. Preferably said milk(s) are heat-treated, typically pasteurized, to ensure sterility. Preferably, said heat treatment is carried out prior to the preparation of the fermented dairy composition.

Preferably, said milk comprises one or more of skimmed, partially-skimmed or non-skimmed milk. Preferably, said milk or milks may be in liquid, powdered and/or concentrated form. In one embodiment, said milk further comprises milk components preferably selected from the group consisting of cream, casein, caseinate (for example calcium or sodium caseinate), whey proteins notably in the form of a concentrate (WPC), milk proteins notably in the form of a concentrate (MPC), milk protein hydrolysates, and mixtures thereof. In one embodiment, said mixture further comprises plant and/or fruit juices. In one embodiment, said milk or milks may be enriched or fortified with further milk components or other nutrients such as but not limited to vitamins, minerals, trace elements or other micronutrients. However it is particularly preferred that the base is a plant-based (i.e. dairy-free) aqueous vegetal base.

i) Aqueous Vegetal Base

Methods for prepare mixtures of vegetal bases by inoculation of micro-organisms are known in the art.

In one embodiment, the vegetal base is an aqueous suspension comprising water and plant-matter preferably selected from the group consisting of fruits, herbs, spices, flowers, tea and/or combinations or mixtures thereof.

Processes for the preparation of such suspensions are known in the art and typically comprise mixing or combining aqueous solution with the plant matter and heat treating. Optionally, process for preparation may include a step of removing insoluble solids before or after heat treatment, methods for such removal are known in the art and may be carried out by means of filtration, centrifugation and/or decantering.

Preferably the heat treatment is carried out at a temperature of less than or equal to 100° C. for a time sufficient to ensure that the product is safe to consume after fermentation. In embodiments the heat treatment is carried out at 70° C. to 100° C., more preferably 80° C. to 100° C. It is within the scope of the skilled person to adjust the time of heat treatment according to the selected temperature, but such treatments may be carried out for less than about 10, 9, 8, 7, 6 or 5 minutes e.g. about 0.1 to about 10 minutes or about 2 to about 5 minutes.

In embodiments the aqueous vegetal base comprises water in an amount of from 99.99% to 20.0% by weight, preferably 99.99% to 50.0% or more preferably 99.99% to 60.0% or 99.99% to 70.0%.

In embodiments the aqueous vegetal base comprises added sugars in an amount of 0.01% to 10.00% by weight. In embodiments the aqueous vegetal base comprises plant matter in an amount of from 0.01% to 80.00% by weight, preferably 0.01% to 50.00% or more preferably 0.01% to 20.00% or 0.01% to 10.00%.

The aqueous base can for example comprise fruit or a fruit preparation in an amount of from 0.1% to 80.00% by weight, for example from 0.1% to 50.00% or 10.00% to 50.00% by weight. Accordingly in embodiments the vegetal base comprises fruit. Fruit preparations typically comprise fruits, as used herein the term "fruit" refers to any fruit form, including for example full fruits, pieces, purees, concentrates, juices etc.

Examples of fruits include for example lemon, fig, strawberry, peach, apricot, mango, apple, pear, raspberry, blueberry, blackberry, passion, cherry, and mixtures or associations thereof, such as peach-passion.

The fruits can be for example provided as:

fruit juices or concentrates thereof, for example fruit juices concentrated from 2 to 5 times, preferably 3 times, for example aseptic fruit juices, for example strawberry, peach, apricot, mango, raspberry, blueberry or apple fruit purees or mixtures thereof, dried fruit whole, cubes or in pieces, for example dried whole figs or mixtures thereof, frozen fruit whole, cubes or in pieces, for example 10 mm fruit cubes, for example Individual Quick Frozen fruit cubes, for example strawberry, peach, apricot, mango, apple, pear fruit cubes or mixtures thereof, Aseptic fruit cubes, for example 10 mm fruit cubes, for example strawberry, peach, apricot, mango, apple or pear fruit cubes or mixtures thereof, fruit purees or concentrates thereof, for example fruit purees concentrated from 2 to 5 times, preferably 3 times, for example aseptic fruit purees, for example strawberry, peach, apricot, mango, raspberry, blueberry or apple fruit purees or mixtures thereof, single aseptic fruit purees, for example strawberry, raspberry, peach, apricot, blueberry or apple single aseptic fruit purees or mixture thereof, frozen whole fruits, for example Individual Quick Frozen whole fruits, for example blueberry, raspberry or blackberry frozen whole fruits, or mixtures thereof, mixtures thereof.

In one embodiment, the fermented composition according to embodiments of the invention is a water-kefir type composition prepared by the fermentation of an aqueous fruit base. Accordingly, in embodiments, the vegetal base comprises fruit, preferably fruit juice, concentrate, puree and/or combinations or mixtures thereof. The vegetal base may be prepared by combining or mixing the fruit matter with water.

The aqueous base can comprise tea, herbs, flowers and/or combinations or mixtures thereof in an amount of 0.01% to 10.00% by weight, for example from 0.01% to 5.00% by weight or 0.01% to 2.00%.

The tea, herbs and flowers may be in fresh, dried, frozen or freeze dried form or may be in the form of extracts, concentrates or infusions.

In one embodiment, the fermented composition according to embodiments of the invention is a kombucha type composition prepared by the fermentation of an aqueous tea base. Accordingly in embodiments the vegetal base comprises tea. Methods for the preparation of tea are well known in the art. The aqueous tea base may be prepared by the steeping or soaking of tea leaves in water and combining with fruit and/or added sugars to provide a fermentable base. The tea may be black, white, green or red and may be in fresh or dried form. The tea leaves may be whole, ground and/or powdered. In an alternative embodiment the aqueous tea base may be provided by dilution of a tea extract and/or liquid concentrate in water.

In embodiments of the invention, the vegetal base does not comprise soy, nuts, seeds, grains and/or combinations or mixtures thereof. Particularly preferred is a base free from, or do not comprise, added sugar, where the total carbohydrate content of the vegetal base is derived from plant-matter selected from the group consisting of fruits, herbs, flowers, tea and/or combinations or mixtures thereof.

The fermented composition may optionally comprise other ingredients such as fermentation aids (such as yeast extract or polypeptides), emulsifiers, stabilizing and flavoring agents. Other ingredients may also include nutritional supplements, vitamins, minerals, trace elements or other micronutrients. such as vitamin A, vitamin B2, vitamin B12, vitamin D, vitamin E, zinc, fiber, protein, calcium, potassium, phosphorus, fatty acids, (e.g., omega 3, omega 6, etc.). Micro-Organisms ii) and iii)

In embodiments, the micro-organisms ii) bacteria and iii) yeast are provided as inoculum suitable for the direct inoculation into, and fermentation of, the aqueous base, typically without the need for a culture step prior to the said direct inoculation. The micro-organisms ii) bacteria and iii) yeast may be inoculated sequentially or concurrently, and may be provided as an inoculum mixture thereof. Typically, the inoculum further comprises excipient or carriers, the selection of which is within the scope of the skilled person but may include buffers or culture media. The inoculum may optionally comprise further components such as cryoprotectants, preservatives and/or additives including nutrients such as yeast extracts, cysteine, sugars and vitamins.

In embodiments, the inoculum is fresh, frozen, dried or lyophilized. The inoculum may be in liquid, dry, spray-dried or solid form. It is particularly preferred that the inoculum is in granular or liquid form. The inoculum may be defrosted and/or dispersed in liquid (e.g. water) prior to inoculation.

In embodiments, the bacteria and yeast are not physically joined by an extracellular matrix secreted by said microorganisms, such as a cellulose biofilm (e.g. kombucha "mother" or SCOBY, for Symbiotic Community of Bacteria and Yeast) or polysaccharide matrix grains (such as but not limited to dairy kefir grains or water kefir grains).

In embodiments, the yeast comprises 1, 2 or more species of the genera selected from the group consisting of *Brettanomyces, Hansenispora, Torulaspora* and *Saccharomyces* and/or mixtures or combinations thereof. In further embodiments, the yeast comprises 1, 2 or more species selected from the group consisting of *Brettanomyces bruxellensis, Hanseniaspora osmophila, Hanseniaspora valbyensis, Torulaspora* sp., *Saccharomyces cerevisiae* and *Saccharomyces uvarum* and/or mixtures or combinations thereof. It is particularly preferred that the yeast is *Saccharomyces cerevisiae.*

In embodiments the bacteria further comprises 1, 2 or more species of the genera selected from the group consisting of *Gluconobacter, Oenococcus, Acetobacter, Bacillus, Lactobacillus* and *Lactococcus* and/or mixtures or combinations thereof. In further embodiments the bacteria comprises 1, 2 or more species selected from the group consisting of *Gluconobacter cerinus, Oenococcus kitaharae, Acetobacter Malorum, Acetobacter Lambici, Bacillus coagulans, Lactobacillus nagelii, Lactobacillus paracasei, Lactobacillus hilgardii, Lactobacillus hordei, Lactobacillus plantarum, Lactococcus lactis lactis, Lactococcus lactis cremoris* and *Lactococcus taiwanensis* and/or mixtures or combinations thereof.

b) Fermentation

Fermentation of the mixture is carried out by incubating the mixture at a temperature suitable for the metabolization of the base by the bacteria to provide a reduction in pH and/or sugar. Suitable temperatures for such fermentation are typically about 20° C. to about 45° C., more preferably about 25° C. to about 35° C. and the temperature is maintained for an incubation time sufficient to provide the desired reduction in pH and/or sugar. In embodiments of the invention fermentation may be carried out under pressure of e.g. up to 1 bar, 2 bar or 3 bar.

In embodiments of the invention, fermentation may be carried out under aeration or oxygenation of the mixture.

In embodiments of the invention, fermentation may be carried out under agitation of the mixture.

Preferably, the fermented composition is prepared by culture of the mixture to provide a reduction in pH, preferably to a pH equal to or lower than 5, 4.5, 4.0 or 3.5. In other embodiments, the fermentation is carried out to a pH preferably between about 4 and about 2.5, and more preferably between about 3.5 and about 2.5.

Preferably, the fermented composition is prepared by culture of the mixture to provide a reduction in sugar to about 0.1%-10.0% w/w sugar, in embodiments 1.0%-5.0% w/w sugar, more preferably 2.0%-4.0% w/w.

Preferably, the fermented composition is prepared by culture of the mixture at a suitable temperature with the microorganisms to provide the required reduction in pH and sugar levels, preferably by culturing for less than or equal to about 72, 48, 36 or 24 hours.

The pH and/or sugar can be adjusted by controlling the fermentation by the microorganism and stopping it when appropriate. The fermentation is stopped, for example, by cooling when the desired target pH and/or sugar levels are reached. Preferably, a stage of cooling of the fermented composition is performed such that the temperature at the end of the cooling is less than about 22° C. preferably about 4° C. to about 10° C.

Optionally the fermented mixture may be carbonated with $CO_2$ gas prior to packaging to provide a product having a dissolved $CO_2$ content of 0.1-10 g/L, 1-7 g/L or 2-5 g/L.

Optionally the product may be packaged into a suitable container. Preferably, the fermented composition, according to embodiments of the invention is provided in a sealed or sealable container containing about 50 ml (or 50 g) to 2 L (or 1 kg), for example a container of 50 ml (or 50 g) to 80 ml (or 80 g), or 80 ml (or 80 g) to 100 ml (or 100 g), or 100 ml (or 100 g) to 125 ml (or 125 g), or 125 ml (or 125 g) to 150 ml (or 150 g), or 150 ml (or 150 g) to 200 ml (or 200 g), or 200 ml (or 200 g) to 250 ml (or 250 g), or 250 ml (or 250 g) to 300 ml (or 300 g), or 300 ml (or 300 g) to 500 ml (or 500 g), or 500 ml (or 500 g) to 750 ml (or 750 g), or 750 ml (or 750 g) to 1 l (or 1 kg), or 1 l (or 1 kg) to 2 l (or 2 kg) product by volume (or weight).

In other embodiments, the fermented composition is provided in a sealed or sealable container containing about 50 ml to 500 ml, 60 ml to 500 ml, 70 ml to 500 ml, 75 ml to 500 ml, 80 ml to 500 g, 85 ml to 500 ml, 90 ml to 500 ml, 95 ml to 500 ml, 100 ml to 500 ml, 105 ml to 500 ml, 110 ml to 500 ml, 115 ml to 500 ml, 120 ml to 500 ml, 125 ml to 500 ml, 130 ml to 500 ml, 135 ml to 500 ml, 140 ml to 500 ml, 45 ml to 5 ml, 150 ml to 500 ml, 200 ml to 500 ml, 300 ml to 500 ml, 320 ml to 500 g or 500 g product by weight. In other embodiments, the fermented composition is provided in a sealed or sealable container containing about 1 oz to 12 oz, 2 oz to 12 oz, 3 oz to 12 oz, 4 oz to 12 oz, 5 oz to 12 oz, 6 oz to 12 oz or 12 oz product by volume.

The container can be any suitable composition container, such as a cup, a can, a bottle, a carton or "brick" packaging, or a flexible container such as a pouch. The container is the packaging of the fermented composition. The container typically presents an opening and a body. The opening can be sealed by sealing means such as a cap, a flexible lid or a rigid lid. In one embodiment the opening and/or sealing means is a tearable or detachable part of the container.

The container can be made of a material, optionally layered, comprising plastics, preferably recyclable and/or recycled, paper and/or metal, or glass.

The invention will be further illustrated by the following non-limiting Examples.

EXAMPLES

Example 1: *Acetobacter* Antibiotic Screening

In order to establish the typical antibiotic resistance profiles of *Acetobacter* a selection of 39 strains was selected from the Danone Culture Collection. Representative strains were selected from the species *orientalis, fabarum, lovaniensis, syzygii, ghanensis, cerevisiae, malorum* and *cibinongensis*. Antibiotic resistance was measured using MICs (minimum inhibitory concentrations) determined according to the ISO 10932 2010 method. For each strain a repetition was carried out (2 measurements made) based on a method of micro-dilutions in liquid medium. The antibiotic MICs were determined using VetMIC microplates and were expressed in μg/mL. Antibiotic resistance profiles were determined for gentamicin, kanamicin, streptomicin, tetracycline, erythromicin, clindamicin, chloramphenicol, ampicilin, vancomicin, neomicin, virginiamicin, ciprofloxacine, lincosamide, rifampicine, trimetroprime, peniciliin, colistine and fosfomicin.

*Acetobacter malorum* CNCM I-5329 was characterized in having a favourable (i.e. sensitive) antibiotic resistance as compared to that typical for the representative 39 species.

Example 2: Acetic Acid Test

The ability of the strain to convert ethanol to acetic acid, and thus its potential for preparation of kombucha and vinegar was determined using a test of acidification in an ethanol base. A fermentation base was prepared by mixing organic cane sugar 50 g per liter water, yeast extract (Biospringer™) 0.2 per liter water with dechlorinated osmosed water. The mixture was heat treated at 90° C. for 5 minutes and sterilized absolute ethanol 1% v/v was added. The base was inoculated with *Acetobacter malorum* CNCM I-5329 at 0.02 v/v. Fermentation was carried out at 30° C. with constant agitation and aeration at 0.1 VVM.

Acetic acid reached the target of 3 g/L in just over 24 hours, thus indicating its suitability for the preparation of kombucha type beverages.

Example 3: Kombucha Type Beverage Preparation (Kieselguhr Clarification)

An aqueous vegetal base was prepared by mixing 0.6 g/L black tea (Naturex™), 50 g/L raw cane sugar, yeast extract (Biospringer™) 0.2 g/L, 94.9 g/L, the base was then heat treated at 95° C. for 3 minutes and cooled to 30° C. The aqueous base was inoculated by mixing dried yeast (Lesaffre™ Oeno CK-S102) 0.001% v/v and lyophilized *Acetobacter* (CNCM I-5329) 0.02% v/v. Fermentation was carried out at 30° C. under 1 bar pressure with oxygenation at 0.1 VVM. Fermentation was carried out until pH was below 3.5, typically in the target range of 2.8-3.2 (about 32 hours). Fermentation was stopped by rapid cooling to 6° C. A fraction of the cooled fermented product was then clarified by means of a kieselguhr process and then the filtered fraction was recombined with a non-filtered fraction to achieve a target micro-organism content of yeast $10^4$-$10^5$ CFU/ml and a bacterial content of above $10^3$ CFU/ml.

Flavouring agents were injected into the beverage and a final step of carbonation was carried out at 0.7 bar pressure to achieve a target of 3-5 g/L dissolved $CO_2$ before bottling and storage at 6° C.

The final product had an ethanol content of less than 0.5% v/v and an acetic acid content of 3 g/L and target CFU was maintained over at least 2 months of storage.

Example 4: Kombucha Type Beverage Preparation (Centrifugation Clarification)

An aqueous vegetal base was prepared by mixing 0.6 g/L black tea (Naturex™), 50 g/L raw cane sugar, yeast extract (Biospringer™) 0.2 g/L, 94.9 g/L, the base was then heat treated at 95° C. for 3 minutes and cooled to 30° C. The aqueous base was inoculated by mixing dried yeast (Lesaffre™ Oeno CK-S102) 0.001% v/v and lyophilized *Acetobacter* (CNCM I-5329) 0.02% v/v. Fermentation was carried out at 30° C. under 1 bar pressure with oxygenation at 0.1 VVM. Fermentation was carried out until pH was below 3.5, typically in the target range of 2.8-3.2 (about 32 hours). Fermentation was stopped by rapid cooling to 6° C. Clarification was carried out on the total volume of fermented product by centrifugation at 8000 g and flow rate adjusted to provide a filtrate having the target micro-organism content of yeast 104-105 CFU/ml and a bacterial content of above 103 CFU/ml. Flavouring agents were injected into the beverage and a final step of carbonation was carried out at 0.7 bar pressure as required to achieve a target of 3-5 g/L dissolved $CO_2$ before bottling and storage at 6° C.

The final product had an ethanol content of less than 0.5% v/v and an acetic acid content of 3 g/L and target CFU was maintained over at least 2 months of storage.

The invention claimed is:

1. A composition comprising a strain deposited at the CNCM under reference number CNCM I-5329, wherein the composition is a fermented compositions.

2. The composition of claim 1, wherein the composition comprises at least $10^1$ CFU/g of CNCM I-5329.

3. The composition according to claim 2, wherein said composition is a plant-based product.

4. The composition according to claim 2, further comprising at least one, two, three or more strains of yeast.

5. The composition according to claim 1, wherein said composition is a food product.

6. The composition according to claim 1, wherein said composition is a fermented beverage.

7. The composition according to claim 6, wherein the fermented beverage is kombucha type beverage, water kefir type beverage, jun type beverage, tibicos type beverage, or a drinking vinegar beverage.

8. The composition according to claim 6, wherein the fermented beverage has a pH between 4 and 2.5.

9. The composition according to claim 1, wherein said composition comprises between $10^2$ to $10^6$ CFU of CNCM 1-5329 per gram of composition.

10. A method for the preparation of a fermented food composition comprising
   a) providing a mixture comprising:
      i) dairy and/or aqueous vegetal base,
      ii) bacteria comprising CNCM I-5329, and
      iii) optionally yeast,
   b) fermenting the mixture to provide a reduction in pH and/or sugar, and
   c) optionally packaging the fermented product.

11. The method according to claim 10, wherein the mixture comprises at least one, two, three or more strains of bacteria.

12. The method according to claim 10, wherein the bacteria are provided in the form of a fresh, frozen, dried or lyophilized inoculum and/or combinations thereof.

* * * * *